United States Patent [19]

Jaedicke et al.

[11] 4,209,450
[45] Jun. 24, 1980

[54] INTRODUCTION OF A CARBONYL GROUP INTO A CYCLOHEXENE RING

[75] Inventors: Hagen Jaedicke, Ludwigshafen; Joachim Paust, Neuhofen, both of Fed. Rep. of Germany

[73] Assignee: BASK Aktiengesellschaft, Fed. Rep. of Germany

[21] Appl. No.: 868,272

[22] Filed: Jan. 10, 1978

[30] Foreign Application Priority Data

Feb. 3, 1977 [DE] Fed. Rep. of Germany ....... 2704406

[51] Int. Cl.$^2$ .......................... C09F 5/08; C11C 3/00; C07C 45/00; C07C 49/00
[52] U.S. Cl. .................... 260/410; 260/413; 560/126; 560/259; 568/378; 568/367; 568/363; 568/356; 568/347; 568/348
[58] Field of Search ........... 260/586 R, 514 L, 514 K, 260/410.9 R, 410.9 M, 410.9 V, 413 L, 413 K, 410 R, 586 P; 560/259, 126

[56] References Cited

U.S. PATENT DOCUMENTS

| | | | |
|---|---|---|---|
| 3,033,897 | 5/1962 | Robeson | 560/259 |
| 3,154,586 | 10/1964 | Bander | 260/586 P |
| 3,646,149 | 2/1972 | Morel | 260/586 P |

OTHER PUBLICATIONS

The Merck Index, Eighth Edition, P 1061.

*Primary Examiner*—John F. Niebling
*Attorney, Agent, or Firm*—Keil & Witherspoon

[57] ABSTRACT

A process for introducing an allyl-positioned carbonyl group into a 2,6,6-trimethylcyclohexene ring which carries a polyenyl radical in the 1-position, by oxidizing the ring with a halogen(V)-oxyacid or a salt of such an acid, and the new oxo compounds obtainable by the said process, which may be used as dyes for foodstuffs or cosmetics. The oxidation is carried out in the presence of a catalyst and of an inert diluent or solvent, in an acid medium. Suitable catalysts are bromine and iodine and the oxides of elements of groups Va, VIa, VIIa and VIII of the periodic table.

7 Claims, No Drawings

INTRODUCTION OF A CARBONYL GROUP INTO A CYCLOHEXENE RING

The present invention relates to a process for introducing an allyl-positioned carbonyl group into a cyclohexene ring by oxidizing an allyl-positioned methylene group or hydroxyl group with a halogen(V)-oxyacid or a salt of such an acid.

The oxidation of retinol, retinal and vitamin A-acid methyl ester with manganese(IV) dioxide so as to bring about oxidation in the 4-position of the cyclohexene ring has been disclosed in Tetrahedron Letters, 1972, pages 1,823–1,825 and J.Chem.Soc. 1957, pages 4,909–4,912. This process requires up to a 20-fold excess of oxidizing agent, based on substrate, and the yields obtained vary greatly, due to the varying activity of the manganese(IV) dioxide, which in turn is a function of its conditions of manufacture.

It has also been disclosed that an allyl-positioned methylene group in the cyclohexene ring can be oxidized by means of metaperiodate. For example, retinal (German Laid-Open Application DOS No. 2,064,495), β-carotin and retro-dehydrocarotin (German Pat. No. 1,793,308) can be respectively converted to 4-oxo-retinal or canthaxanthin by means of sodium metaperiodate in the presence of a halogen or of an oxide of a metal selected from groups Va, VIa, VIIa and VIII of the periodic table. Essential disadvantages of this process are the high cost of the oxidizing agent, and the low yield, varying from 17 to 38%, when manufacturing canthaxanthin.

We have now found that an allyl-positioned carbonyl group may be introduced into a cyclohexene ring by oxidizing a cyclohexene derivative of the formula

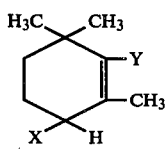

where X is hydrogen or hydroxyl and Y is a polyenyl radical, with a halogen(V)-oxyacid or a salt of such an acid in the presence of bromine or iodine or of an oxide of an element selected from groups Va, VIa, VIIa and VIII of the periodic table, as the catalyst, and in the presence of an inert diluent or solvent, in an acid medium at from 0° to 100° C.

Essential advantages of the process according to the invention are that the reaction takes place rapidly, the yield is improved and the oxidizing agents are readily accessible and cheap.

Suitable starting compounds of the formula I are cyclohexene derivatives which carry allyl-positioned methylene or hydroxymethylene groups and have a polyenyl radical as the substituent Y, as well as β-ionone.

The end products are polyene compounds of the formula II

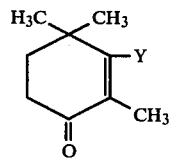

where Y is

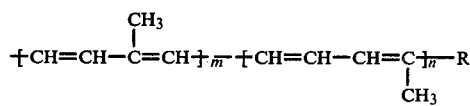

where m is 0, 1 or 2 and n is 0, 1, 2, 3 or 4 and R is methyl, formyl, carboxyl, alkanoyl of 2 to 4 carbon atoms, alkoxycarbonyl of 2 to 4 carbon atoms, alkoxymethyl of 2 to 4 carbon atoms, alkanoyloxymethyl of 3 or 4 carbon atoms, β-acetylvinyl, β-formylvinyl or β-(2,6,6-trimethyl-cyclohex-1-en-3-onyl)-vinyl, with the proviso that m and n are not both 2 if R is β-(2,6,6-trimethylcyclohex-1-en-3-onyl)-vinyl.

Examples of starting materials are β-ionone for the manufacture of 4-oxo-β-ionone, vitamin A acetate for the manufacture of 4-oxo-vitamin A acetate, β-apo-8'-carotinal for the manufacture of 4-oxo-β-apo-8'-carotinal, β-apo-12'-carotinal for the manufacture of 4-oxo-β-apo-12'-carotinal, β-apo-4'-carotinic acid ethyl ester for the manufacture of 4-oxo-β-apo-4'-carotinic acid ethyl ester, β-apo-8'-carotinic acid ethyl ester for the manufacture of 4-oxo-β-apo-8'-carotinic acid ethyl ester, citranaxanthin for the manufacture of 4-oxo-citranaxanthin, torularhodinaldehyde for the manufacture of 4-oxo-torularhodinaldehyde, torularhodine methyl ester for the manufacture of 4-oxo-torularhodine methyl ester, β-apo-2'-carotinal for the manufacture of 4-oxo-β-apo-2'-carotinal, torularhodine for the manufacture of 4-oxo-torularhodine, torulene for the manufacture of 4-oxo-torulene, 7',8'-dihydro-7'-apo-β-carotin-8'-one for the manufacture of 4-oxo-7',8'-dihydro-7'-apo-β-carotin-8'-one and all-trans-1,10-di-(2,6,6-trimethylcyclohex-1-enyl)-3,8-dimethyl-deca-1,3,5,7,9-pentaene for the manufacture of all-trans-1,10-di-(2,6,6-trimethylcyclohex-1-en-3-onyl)-deca-1,3,5,7,9-pentaene.

The starting materials are oxidized in the form of solutions. The use of solutions in readily volatile diluents or solvents which are water-immiscible is preferred.

Suitable diluents and solvents include aliphatic chlorohydrocarbons, eg. chloroform, methylene chloride, 1,1-dichloroethane, 1,2-dichloroethane, 1,1,2-trichloroethane, 1,1,2,2-tetrachloroethane, 1,2-dichloroethylene and 1,1,2-trichloroethylene, aromatic hydrocarbons, eg. benzene, toluene, nitrobenzene and chlorobenzene, dialkyl ethers, eg. diethyl ether and di-n-propyl ether, and carbon disulfide. Particularly suitable solvents are chloroform, methylene chloride and 1,2-dichloroethane. Mixtures of these diluents or solvents may also be used.

Suitable oxidizing agents are halogen(V)-oxyacids or salts of these acids. They include chloric acid, bromic acid, iodic acid and the alkali metal salts, alkaline earth metal salts and ammonium salts of these acids, especially chloric acid and bromic acid and their alkali metal salts. The oxidizing agents are advantageously added to the reaction mixture in the form of their aqueous solutions of from 5 to 50% strength by weight. The molar ratio of oxidizing agent to starting material is generally from 1:1 to 20:1, preferably from 1:1 to 10:1. A more than 20-fold molar excess of oxidizing agent has no effect on the reaction.

The oxidation is catalyzed by bromine or iodine or by an oxide of an element selected from group Va, VIa, VIIa or VIII of the periodic table. Examples of suitable catalysts are vanadium pentoxide, molybdenum trioxide, tungsten trioxide, manganese dioxide, nickel oxide and osmium tetroxide. Preferred catalysts are bromine, iodine and osmium tetroxide. Iodine is a particularly suitable catalyst.

The catalyst is added undiluted or in solution, for example in the solvent which has been used for the solution of the starting material or in water. The catalyst may also advantageously be formed in situ; for example iodine is formed from sodium iodine under the reaction conditions. The amount of catalyst is advantageously from 0.1 to 25% by weight, based on starting material. Larger amounts of catalyst have no additional effect on the reaction.

The reaction is carried out at from 0° to 100° C., preferably from 10° to 70° C. The reaction temperature may be varied within wide limits, the upper limit being determined by the heat stability of the starting material or of the end product.

The reaction takes place in an acid medium, ranging from strongly acid to pH 7. The preferred pH range is from 1 to 3. The desired pH may be obtained by means of acids, eg. sulfuric acid, hydrochloric acid or acetic acid, or of buffer mixtures.

The reaction time is generally from 1 to 24 hours, depending on the selected conditions.

In order to prevent further oxidation of the end products by atmospheric oxygen, the reaction may be carried out under an inert gas atmosphere. Gases which are suitably inert under the reaction conditions are argon, neon, helium, carbon dioxide and especially nitrogen.

In a preferred embodiment of the process, an aqueous solution of the oxidizing agent is added, under an inert gas atmosphere, to a solution or slurry of the starting material in a diluent or solvent which is inert under the reaction conditions and is water-immiscible. The aqueous phase is then brought to the desired pH by means of an acid or a buffer mixture. The catalyst is added as a solid or solution and the two phases are mixed by stirring until a suitable analytical method, eg. thin layer chromatography, indicates complete conversion.

The organic phase is then stripped off and crude end product is isolated therefrom either by stripping off the solvent or by precipitation. Normally, it suffices to boil the crude material in a solvent which does not dissolve the end product, eg. in an alcohol, in order to obtained a crystalline end product. The reaction product may or may not be purified by chromatography.

The Examples which follow illustrate the process according to the invention.

EXAMPLE 1

9.6 g (0.05 mole) of β-ionone are dissolved in 250 ml of chloroform. 26.5 g (0.25 mole) of sodium chlorate and 1.125 g of sodium iodide in 100 ml of water are added. The mixture is acidified with 0.11 ml of concentrated sulfuric acid and stirred for 24 hours at 45° C. It is then allowed to cool, the phases are separated and the chloroform phase is washed first with saturated sodium bicarbonate solution and then with water. After stripping off the solvent, 9.1 g of a dark oil, containing 64% by weight of 4-oxo-β-ionone, remain. Fractional distillation in a high vacuum gives 4.1 g of an oil which solidifies slowly. After recrystallization from a 1:1 mixture of methanol and water, the product has a melting point of 51°-52° C. and proves identical, in all properties, with the product obtained by reacting β-ionone with N-bromo-succinimide and then carrying out an oxidation with manganese (IV) dioxide (J.Chem.Soc. (1951), 1074).

EXAMPLE 2

1 g of 4-hydroxy-β-apo-8'-carotinic acid methyl ester, prepared as described in U.S. Pat. No. 3,068,257, is dissolved in 30 ml of chloroform. A solution of 1 g of sodium chlorate and 0.1 g of osmium tetroxide in 10 ml of water is added and the mixture is stirred at 10° C. It is acidified with 1 drop of acetic acid and the phases are agitated for 24 hours. They are then separated, the organic phase is washed with water and dried, and the solvent is distilled off under reduced pressure. The partially crystalline residue is refluxed with 50 ml of heptane for 60 minutes. After cooling and standing for 24 hours, 0.61 g of 4-oxo-β-apo-8'-carotinic acid methyl ester is filtered off.

EXAMPLE 3

0.1 mole of vitamin A acetate is introduced into 850 ml of methylene chloride. A solution of 79.5 g of sodium chlorate (0.75 mole) and 1.125 g (7.51 mmoles, corresponding to 7.5 mole %, based on vitamin A acetate) of sodium iodide in 300 ml of water is added. After cooling to 10° C., the mixture is acidified with 0.015 g of concentrated sulfuric acid and is stirred at 10° C. for 18 hours. The phases are then separated and the organic phase is washed with 400 ml of saturated sodium bicarbonate solution and then with water. After drying and concentrating, an oily raw material which contains 57% by weight of 4-oxo-vitamin A acetate is obtained. The ketone can be obtained pure by column chromatography.

220 Mc/s—$^1$H—NMR spectrum (CDCl$_3$); δ values: 1.4 s (6H); 1.8 s (3H); 2.5 t (2H); 6.1–6.7 m (5H).

Mass spectrum: m/e: 282 (M—CH$_3$COOH); 43 (H$_3$C—CO).

IR spectrum: bands at 1,735 cm$^{-1}$ and 1,655 cm$^{-1}$.

EXAMPLE 4

5 g of β-apo-12'-carotinal are dissolved in 100 ml of 1,2-dichloroethane. A solution of 4 g of sodium chlorate and 0.3 g of sodium iodide in 80 ml of water is added. The mixture is heated to the reflux temperature, stirred and acidified with 1 ml of aqueous hydrochloric acid which contains 3 mg of hydrogen chloride. After 4 hours, the mixture is allowed to cool to room temperature. After separating the phases, the organic solution of the carotinoid is washed with water, with a dilute sodium carbonate solution and again with water. After drying over magnesium sulfate, the solvent is evaporated off under reduced pressure. A viscous red oil remains, from which 3.45 g of crystalline 4-oxo-β-apo-12'-carotinal are obtained by boiling in 20 ml of isobutanol, cooling and filtering after 24 hours.

220 Mc/s—$^1$H—NMR spectrum (CDCl$_3$); δ values: 1.25 s (6H); 1.9 s (6H); 2.1 d (6H); 2.55 t (2H); 6.2–7.3 m (9H); 9.5 s (1H).

IR spectrum: band at 1,650 cm$^{-1}$.

UV spectrum: $\lambda_{max}=415$ nm in cyclohexane; $E_1^1=2,360$.

EXAMPLE 5

10 g of β-apo-8'-carotinic acid ethyl ester are dissolved in 250 ml of methylene chloride and the solution is cooled to 10° C. 8 g of sodium chlorate and 0.2 g of sodium iodide, dissolved in 100 ml of water, are added. When both phases have reached 10° C., 0.12 ml of acetic acid dissolved in 20 ml of water is added dropwise in the course of 60 minutes. After stirring for 10 hours at 10° C., half the starting material has reacted. A further 0.2 g of sodium iodide and 0.12 ml of acetic acid dissolved in 20 ml of water are added and the mixture is stirred for a further 12 hours at room temperature. It is worked up as described in Example 2 and the crude material, in 30 ml of ethanol, is refluxed for 10 hours. After cooling, 6.15 g of 4-oxo-β-apo-8'-carotinic acid ethyl ester, of melting point 142°–143° C., are filtered off after 24 hours.

220 Mc/s—$^1$H—NMR spectrum (CDCl$_3$); δ values: 1.15 s (6H); 1.3 s (3H); 1.95 s (12H); 2.5 t (2H); 4.2 q (2H); 6–6.7 m (11H); 7.25 d (1H).

US spectrum: $\lambda_{max}=450$ nm in cyclohexane; $E_1^1=2,220$.

EXAMPLE 6

10 g of β-apo-4'-carotinic acid ethyl ester are oxidized as described in Example 4. The mixture is stirred for 10 hours at 10° C. and worked up without adding further catalyst or acid. After boiling in ethanol, and cooling, 7.96 g of 4-oxo-β-apo-4'-carotinic acid ethyl ester are isolated.

220 Mc/s—$^1$H—NMR spectrum (CDCl$_3$); δ values; 1.2 s (6H); 1.3 t (3H); 2.5 t (2H); 4.2 g (2H); 6.1–6.7 m (14H); 7.25 d (1H).

US spectrum: $\lambda_{max}=481$ nm in cyclohexane; $E_1^1=2,310$.

EXAMPLE 7

10 g of β-apo-8'-carotinal are dissolved in 200 ml of 1,2-dichloroethane. 12 g of sodium chlorate and 0.5 g of sodium bromide in 100 ml of water are added and the mixture is heated to the reflux temperature. 10 ml of aqueous hydrochloric acid containing 3 mg of hydrogen chloride are added dropwise in the course of 60 minutes, whilst stirring. Refluxing is continued for 60 minutes and the mixture is then cooled. After separating the phases, the organic phase is repeatedly washed with water and then concentrated. 30 ml of isopropyl alcohol are added to the oily crude product and the mixture is refluxed for 2 hours. After 24 hours, 7.14 g of crystalline 4-oxo-β-apo-8'-carotinal, of melting point 152° C., are filtered off.

220 Mc/s—$^1$H—NMR spectrum (CDCl$_3$): δ values: 1.2 s (6H); 1.8 s (8H); 2.0 s (9H); 2.5 t (2H); 6.15–6.95 m (12H); 9.45 s (1H).

UV spectrum: $\lambda_{max}=449$ nm in cyclohexane; $E_1^1=2,750$.

Polyene compounds of the formula II where Y is $$\left[-CH=CH-\underset{\underset{CH_3}{|}}{C}=CH-\right]_m \left[-CH=CH-CH=\underset{\underset{CH_3}{|}}{C}-\right]_n R$$

where m is 1 or 2 and n is 0, 1, 2, 3 or 4 and R is methyl, formyl, carboxyl, alkanoyl of 2 to 4 carbon atoms, alkoxycarbonyl of 2 to 4 carbon atoms, alkoxymethyl of 2 to 4 carbon atoms, alkanoyloxymethyl of 3 to 4 carbon atoms, β-formylvinyl or β-(2,6,6-trimethylcyclohex-1en-3-onyl)-vinyl, with the proviso that n is not 0 if R is formyl, carboxyl or methoxycarbonyl and m and n are not both 2 if R is β-(2,6,6-trimethylcyclohex-1-en-3-onyl)-vinyl, are new.

They are red and can be used as dyes for foodstuffs and cosmetics. They can also serve as valuable intermediates for the manufacture of carotinoids. Eg. the 4-oxo-aldehydes (of 25 or 30 carbon atoms) may be used for the manufacture of echinenone.

The Examples which follow illustrate the use of the compounds.

EXAMPLE 8

A lipophilized starch is prepared from rice starch by means of an aqueous solution of dimethyl-stearyl-benzylammonium chloride. 4-Oxo-β-apo-8'-carotinic acid ethyl ester is then worked into the starch in the conventional manner. The pasty slurry obtained is dried and ground to give a powder, which is added to a talc composition, giving a talc with a hue resembling skin color.

EXAMPLE 9

A 10% strength, cold water-soluble, dry powder formulation of 4-oxo-β-apo-8'-carotinal is prepared in the conventional manner. 1 g of this dye formulation is dissolved in 10 ml of water and added to the raw materials required for 10 liters of ice cream, eg. cream, milk, sugar, gelatin and flavoring. A deep red ice cream is obtained.

EXAMPLE 10

100 mg of a dye formulation containing 10% of 4-oxo-β-apo-4'-carotinic acid ethyl ester are added to a blancmange powder which suffices for one liter of finished blancmange, and the powder is then used in the conventional manner by stirring or boiling with milk.

EXAMPLE 11

0.5 g of a dry powder containing 10% of 4-oxo-β-apo-12'-carotinal is dissolved in 10 ml of water and the solution is homogeneously incorporated into 1 kg of white toothpaste of a conventional composition. Alternatively, the same dye formulation may be added to the raw materials which are dissolved in water or pasted with water. A red toothpaste is obtained.

EXAMPLE 12

3.98 g of 4-oxo-β-apo-12'-carotinal (4-oxo-aldehyde of 25 carbon atoms) are added to a solution of 5.62 g of β-ionylidene ethyl-triphenyl-phosphonium bisulfate in 67 ml of absolute dimethylformamide. The mixture is cooled to −20° C. and at this temperature 0.92 g of ammonia gas is introduced in the course of one hour, whilst stirring. The mixture is then allowed to come to room temperature, 34 ml of water and 40 ml of heptane are added and the batch is stirred briefly at 40° C. The lower phase is then separated off until the carotinoid present at the interface is encountered, and 80 ml of water are added. The mixture is stirred at 40° C. and the lower phase is again separated off. The upper phase is then washed twice with a mixture of 30 ml of methanol and 20 ml of water and is dehydrated azeotropically, and the heptane is distilled off until the residual volume is 10 ml. The residue is refluxed for 10 hours. When it has cooled, 80 ml of heptane are added and the mixture is filtered. 3.76 g of a finely crystalline residue comprising 97% of all-trans-echinenone are obtained.

We claim:

1. A process for introducing an allyl-positioned carbonyl group into a cyclohexene ring, wherein a cyclohexene derivative of the formula

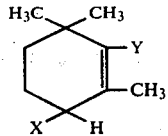

where X is hydrogen or hydroxyl and Y is a polyenyl radical, is oxidized with a halogen(V)-oxyacid or a salt of such an acid in the presence of bromine or iodine or of an oxide of an element selected from groups Va, VIa, VIIa and VIII of the periodic table, as the catalyst, and in the presence of an inert diluent or solvent, in an acid medium at from 0° to 100° C.

2. A process as claimed in claim 1, wherein the oxidation is carried out with an alkali metal salt of chloric acid or of bromic acid.

3. A process as claimed in claim 1, wherein the oxidation is carried out in the presence of iodine as the catalyst.

4. A process as claimed in claim 3, wherein the catalyst is formed in situ.

5. A process as claimed in claim 1, wherein the oxidation is carried out in the presence of an inert diluent or solvent which is water-immiscible.

6. A process as claimed in claim 1, wherein the oxidation is carried out in the presence of an aliphatic chlorohydrocarbon as the diluent or solvent.

7. A polyene compound of the formula

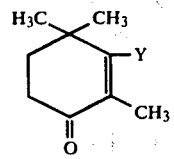

where Y is

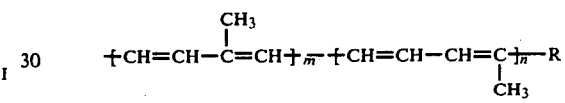

where m is 1 or 2 and n is 0, 1, 2, 3 or 4 and R is methyl, carboxyl, alkanoyl of 2 to 4 carbon atoms, alkoxycarbonyl of 2 to 4 carbon atoms, alkoxymethyl of 2 to 4 carbon atoms, alkanoyloxymethyl of 3 or 4 carbon atoms, β-formylvinyl or β-(2,6,6-trimethyl-cyclohex-1-en-3-onyl)-vinyl, with the proviso that n is not 0 if R is carboxyl or methoxycarbonyl, and m and n are not both 2 if R is β-(2,6,6-trimethylcyclohex-1-en-3-onyl)-vinyl.

* * * * *